(12) United States Patent
Ong et al.

(10) Patent No.: US 9,689,805 B2
(45) Date of Patent: *Jun. 27, 2017

(54) SYSTEMS AND METHODS ELIMINATING FALSE DEFECT DETECTIONS

(71) Applicant: Taiwan Semiconductor Manufacturing Company, Ltd., Hsin-Chu (TW)

(72) Inventors: Biow-Hiem Ong, Singapore (SG); Chih-Chiang Tu, Tauyen (TW); Chien-Hung Lai, Taichung (TW); Jong-Yuh Chang, Jhubei (TW); Kuang-Yu Liu, Yuanlin Township, Changhua County (TW)

(73) Assignee: TAIWAN SEMICONDUCTOR MANUFACTURING COMPANY, LTD., Hsin-Chu (TW)

( * ) Notice: Subject to any disclaimer, the term of this patent is extended or adjusted under 35 U.S.C. 154(b) by 28 days.

This patent is subject to a terminal disclaimer.

(21) Appl. No.: 14/746,961

(22) Filed: Jun. 23, 2015

(65) Prior Publication Data

US 2015/0316489 A1 Nov. 5, 2015

Related U.S. Application Data

(63) Continuation of application No. 13/025,709, filed on Feb. 11, 2011, now Pat. No. 9,063,097.

(51) Int. Cl.
 *G01N 21/00* (2006.01)
 *G01N 21/88* (2006.01)
 (Continued)

(52) U.S. Cl.
 CPC ......... *G01N 21/8806* (2013.01); *G01N 21/55* (2013.01); *G01N 21/59* (2013.01);
 (Continued)

(58) Field of Classification Search
 CPC ......... H01L 2924/0002; H01L 2924/00; H01L 22/12; H01L 22/20; G01N 2021/558;
 (Continued)

(56) References Cited

U.S. PATENT DOCUMENTS 5,808,735 A 9/1998 Lee et al.
7,586,607 B2 9/2009 Sun et al.
(Continued)

OTHER PUBLICATIONS

Ooi, M. L., et al., (Jan. 2010). Fast and accurate automatic defect cluster extraction for semiconductor wafers. In Electronic Design, Test and Application, 2010 DELTA'10. Fifth IEEE International Symposium on (pp. 276-280). IEEE.

*Primary Examiner* — Tri T Ton
(74) *Attorney, Agent, or Firm* — Haynes and Boone, LLP

(57) ABSTRACT

A method for inspecting a manufactured product includes applying a first test regimen to the manufactured product to identify product defects. The first test regimen produces a first set of defect candidates. The method further includes applying a second test regimen to the manufactured product to identify product defects. The second test regimen produces a second set of defect candidates, and the second test regimen is different from the first test regimen. The method also includes generating a first filtered defect set by eliminating ones of the first set of defect candidates that are not identified in the second set of defect candidates.

20 Claims, 9 Drawing Sheets

(51) Int. Cl.
*G01N 21/95*       (2006.01)
*G01N 21/59*       (2006.01)
*G01N 21/55*       (2014.01)
*G01N 21/956*      (2006.01)
*H01L 21/66*       (2006.01)

(52) U.S. Cl.
CPC ....... *G01N 21/9501* (2013.01); *G01N 21/956* (2013.01); *G01N 2021/558* (2013.01); *G01N 2021/8809* (2013.01); *H01L 22/12* (2013.01); *H01L 22/20* (2013.01); *H01L 2924/0002* (2013.01)

(58) Field of Classification Search
CPC ........... G01N 2021/8809; G01N 21/55; G01N 21/59; G01N 21/8806; G01N 21/9501; G01N 21/956
USPC ....................... 356/237.1–237.6, 239.1–239.8
See application file for complete search history.

(56) References Cited

U.S. PATENT DOCUMENTS

| | | |
|---|---|---|
| 8,135,207 B2 | 3/2012 | Silberstein et al. |
| 8,274,652 B2 | 9/2012 | Urano et al. |
| 9,063,097 B2* | 6/2015 | Ong ................... G01N 21/956 |
| 2004/0015808 A1 | 1/2004 | Pang et al. |
| 2004/0223639 A1 | 11/2004 | Sato et al. |
| 2005/0129303 A1 | 6/2005 | Smilansky et al. |
| 2006/0242619 A1 | 10/2006 | Pang et al. |
| 2012/0010843 A1 | 1/2012 | Lee et al. |
| 2012/0171600 A1 | 7/2012 | Catey et al. |
| 2012/0207381 A1 | 8/2012 | Ong et al. |

\* cited by examiner

| Key Detectors | Recipe #1 (Middle T/R) | Recipe #2 (High T sensitivity) | Recipe #3 (High R sensitivity) |
|---|---|---|---|
| Transmitted | 80 | 90 | 60 |
| Reflected | 80 | 60 | 90 |

FIG. 4

SYSTEMS AND METHODS ELIMINATING FALSE DEFECT DETECTIONS

PRIORITY INFORMATION

This application is a continuation of U.S. patent application Ser. No. 13/025,709 filed Feb. 11, 2011 and entitled "Systems and Methods Eliminating False Defect Detections," the disclosure of which is hereby incorporated by reference in its entirety.

BACKGROUND

The present disclosure relates generally to manufacturing. Specifically, the present disclosure relates to systems and methods that use multiple defect tests to eliminate false defect identifications.

As time goes on, semiconductor devices generally get smaller, with more transistors and other structures on a single die. As the structures get smaller, testing intermediate tools for making the products and testing the products themselves becomes more challenging. For instance, some photomasks are produced using electron beam writing to shape very fine features onto the masks, where examples of very fine features include Optical Proximity Correction (OPC) features. A conventional testing technique uses a single optical testing recipe that looks at both transmitted and reflected light from the mask and discerns where defects exist in the mask. As the features of masks get smaller, false defect detections typically increase.

In some conventional systems, a first defect detection recipe is created with a baseline sensitivity and then applied to a mask with a known geometry and known defects. The results are examined to see whether the recipe detected all real defects and to see how many false defects were detected. The sensitivity may be adjusted up if not all real defects were detected and may be adjusted down if there was a very high incidence of false detections. The process can be iterative to adjust the sensitivity to a point where all real defects are detected and false defects are minimized as much as possible. Several other recipes may be created and tuned as well.

Some recipes use test processes that are more sensitive to light reflected from a mask while other recipes use test processes that are more sensitive to light transmitted through a mask. Additionally, some testing recipes produce more false defect detections than do other testing recipes. Thus, choosing a single testing recipe for a mask in production can be important since it affects the number of defects, whether real or false, that are detected.

Typically, after defects are detected, a human user goes through the identified defects and discerns which of the defects are real and which are false. Real defects are then repaired before the mask is finished and shipped to a customer.

Choosing a recipe that produces an excessive number of false detections may unnecessarily increase cycle time and cost money. An efficient way to reduce false defect detection is called for.

SUMMARY

The present disclosure provides for many different embodiments. In a first embodiment, a method for inspecting a manufactured product includes applying a first test regimen to the manufactured product to identify product defects. The first test regimen produces a first set of defect candidates. The method further includes applying a second test regimen to the manufactured product to identify product defects. The second test regimen produces a second set of defect candidates, and the second test regimen is different from the first test regimen. The method also includes generating a first filtered defect set by eliminating ones of the first set of defect candidates that are not identified in the second set of defect candidates.

In another embodiment, a computer program product having a computer readable medium tangibly recording computer program logic for indentifying defects in an item of manufacture includes code to inspect the item of manufacture using a first test and code to inspect the item of manufacture using and a second test after inspection using the first test. The first and second tests are different and have different probabilities of producing false defect indications. The computer program product also includes code to eliminate defect indications by the first test that are not identified by the second test.

In another embodiment system for inspecting manufactured goods for defects includes a first testing unit for performing a first test for defects and a second testing unit for performing a second test for defects. The first and second tests are different. The system also includes a false defect detection unit receiving test results from the first and second testing units and eliminating defects that are not found by both the first and the second testing units.

BRIEF DESCRIPTION OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion.

FIG. 4 provides a comparison of three exemplary test recipes is given.

DETAILED DESCRIPTION

Figure 1:
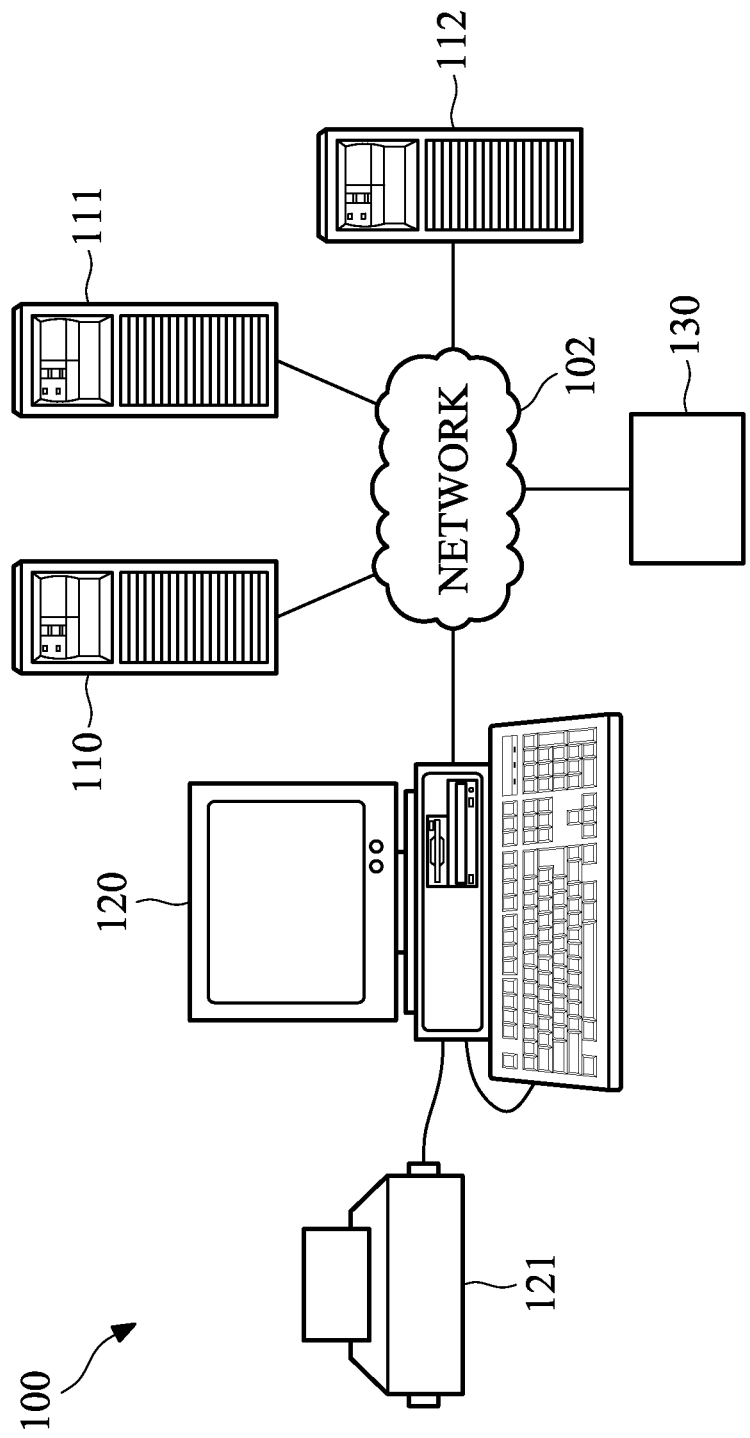
FIG. 1 is a simplified diagram of a network system in which embodiments may be implemented.

The present disclosure relates generally to manufacturing. Specifically, the present disclosure relates to techniques to eliminate or reduce false defect detections. The examples herein discuss applying the techniques to the production of photomasks that have very fine features and present a challenge for testing. However, it is understood that the scope of embodiments can include any system for manufacturing a product that is tested for defects, whether the system involves photomasks or some other manufactured unit.

The following disclosure provides many different embodiments, or examples, for implementing different features of the invention. Specific examples of components and arrangements are described below to simplify the present disclosure. These are, of course, merely examples and are not intended to be limiting. In addition, the present disclosure may repeat reference numerals and/or letters in the various examples. This repetition is for the purpose of simplicity and clarity and does not in itself dictate a relationship between the various embodiments and/or configurations discussed.

With reference now to the figures, FIG. 1 is a simplified diagram of a network system 100 in which embodiments may be implemented. Network system 100 includes a network 102 that provides a medium for communications between various devices and computers communicatively coupled by network system 100. Network 102 may be implemented as one or more of various networks, such as the Internet, an intranet, a local area network, a wide area network (WAN), or another network architecture that facilitates communications between network connected devices. Network 102 may include any one or more of various communication connections, such as wire, wireless, fiber optic, satellite links, or other communication media.

In the present example, various servers 110-112 are connected to network 102. In addition, a client 120 is connected to network 102. Servers 110-112 may be implemented as hypertext transfer protocol (HTTP) servers, file transfer protocol (FTP) servers, application servers, or other devices that provide data sources such as web pages or other content to client 120 connected therewith. Client 120 may be implemented as a personal computer, a portable computer, a network computer, a super computer, or another computational device. Client 120 is interconnected with a local printer 121 and/or a network printer for producing hardcopy output.

Additionally, client 120 is connected to defect testing unit 130, which performs optical defect testing on photomasks and returns results to one or more of computers 110-112, 120. Defect testing unit 130 may include hardware and/or software for performing defect detection, available from, e.g., Applied Materials, Inc., or Lasertec Corporation. Defect testing unit 130 is operable to perform at least three different testing recipes and may include more than one hardware setup as appropriate for performing the different testing recipes. Other embodiments may be operable to apply, two, four, or more testing recipes according to the application.

Defect testing unit 130 provides the results of testing to computers for further processing. Techniques for false defect elimination discussed further below may be performed by one or more computers, such as client 120 and/or servers 110-112. For instance, one or more computers receive testing data, process the testing data, and eliminate false defect detections therefrom. It is not required that various embodiments eliminate all false detections. Rather, it is understood that the scope of embodiments includes systems and methods that eliminate some portion of false defect detections.

Figure 2:
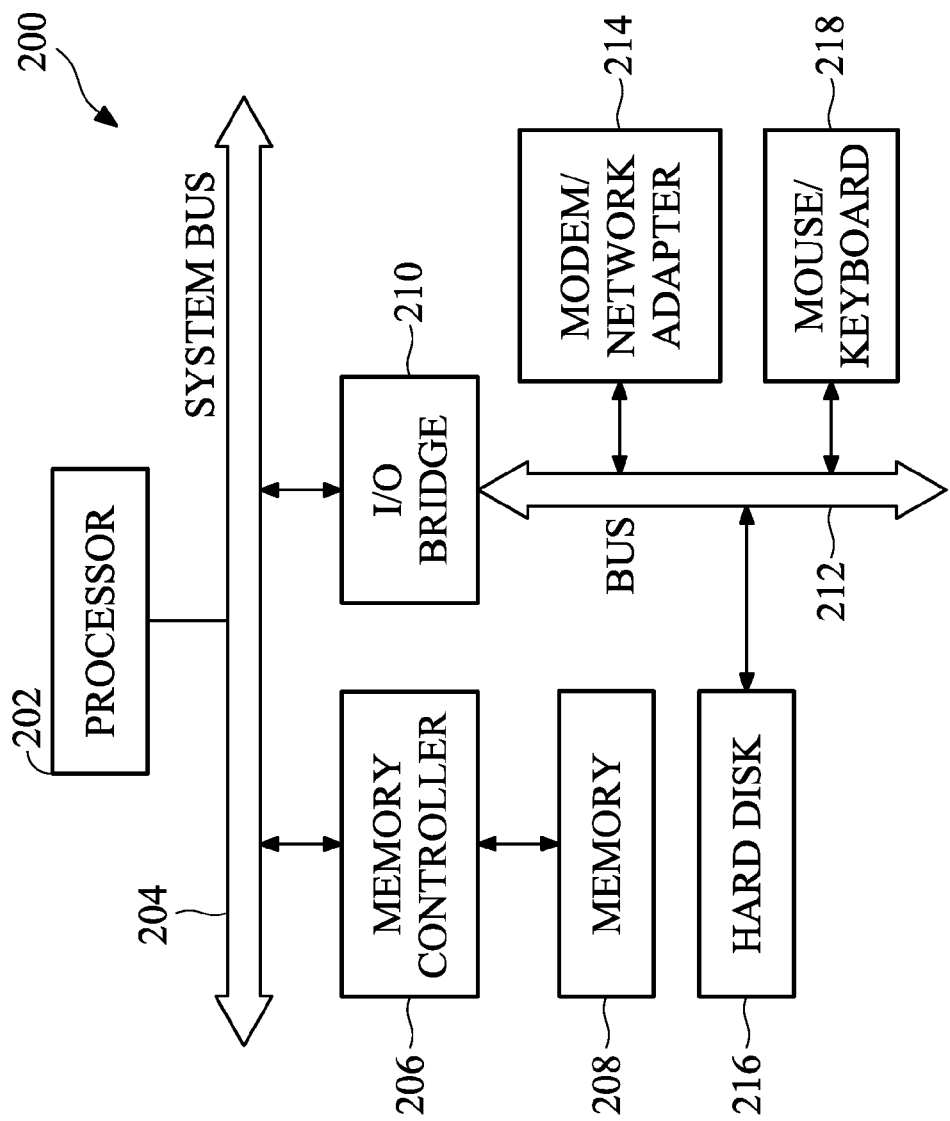
FIG. 2 is a simplified block diagram of a computer system that may be configured to implement embodiments of a defect detection system.

FIG. 2 is a simplified block diagram of a computer system 200, such as client 120 or any of servers 110-112 shown in FIG. 1, that may be configured to implement embodiments of a defect detection system. Computer system 200 includes a processor 202 interconnected with a system bus 204. System bus 204 provides couplings to subsystems and components of computer system 200. A memory controller 206 interconnected with a system memory 208 provides a communicative coupling between memory 208 and processor 202. Memory 208 may store executable instructions that provide testing and/or defect filtering functionality as described more fully below. An input/output bridge 210 may be connected with system bus 204, and one or more input/output devices may be connected with an I/O bus 212. For example, a hard disk 216 (or other memory, such as a flash drive) may provide non-transitory, non-volatile storage, and a modem or network adapter 214 may provide a communication interface that facilitates communication exchanges between computer system 200 and one or more data resources on a network. Additionally, user input devices, such as a mouse/keyboard 218, may be coupled with I/O bus 212 and facilitate user input to computer system 200. The configuration of computer system 200 is illustrative and is chosen only to facilitate an understanding of embodiments described herein.

Figure 3:
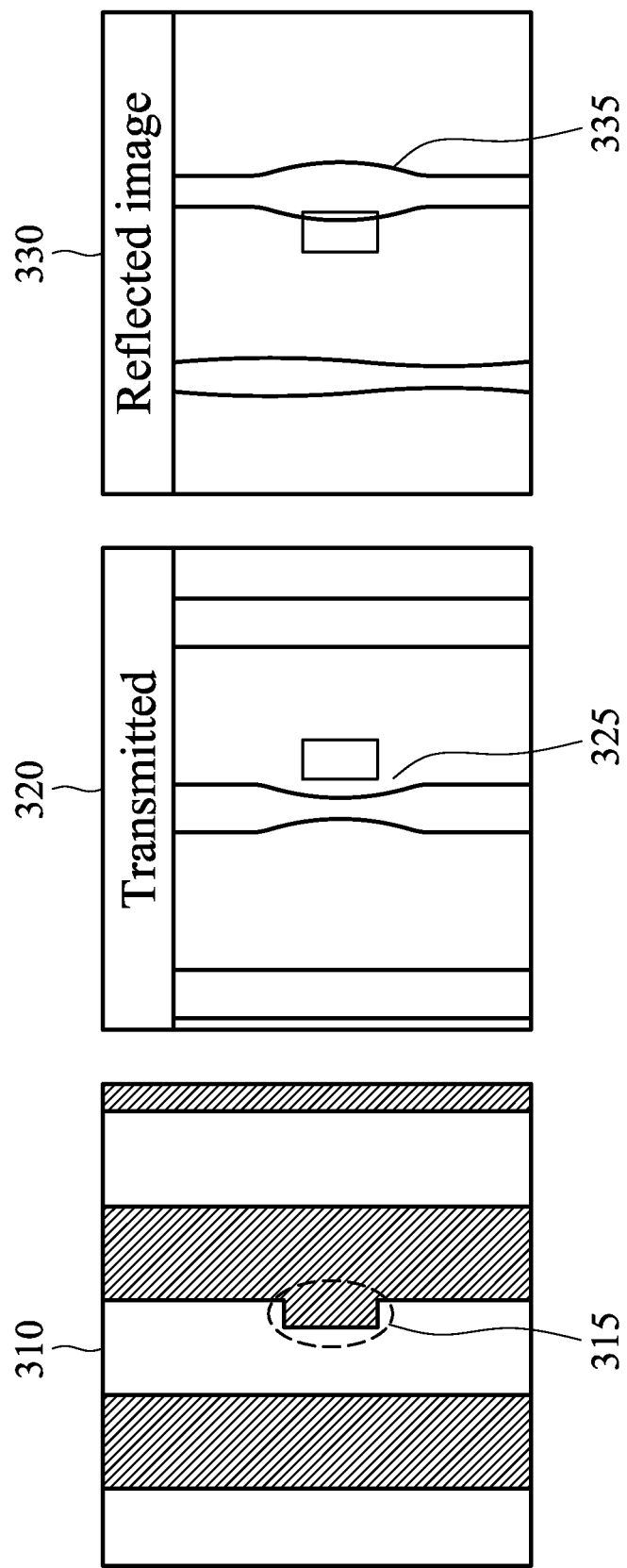
FIG. 3 is an illustration of an exemplary wafer portion as well as images produced during defect testing.

FIG. 3 is an illustration of exemplary wafer portion 310 as well as images 320, 330 produced during defect testing. The wafer has defect 315, and a particular test recipe is applied to detect the defect. Image 320 is an image produced from a test process that uses light transmitted through the mask. Mark 325 shows how the defect appears in transmitted light. Image 330 is an image produced from a test process that uses light reflected from the mask. Mark 335 shows how the defect appears in reflected light. Images 320 and 330 may be produced using the same test recipe or different test recipes.

In this example, a test recipe includes a test process or suite of test processes that is independently able to identify defects. One example of a test process is a critical dimension test that uses visible light to examine contours produced from transmitted or reflected light as the light interacts with geometrical features on the mask. A test image is compared to a reference image to discern whether a dimension of a contour is too small or too big and, if so, a defect is marked at that particular feature. Images 320, 330 of FIG. 3 are test images from an exemplary critical dimension test process. Another example of a test process is a pixel difference detector that compares a reference grayscale pixel map with a pixel map produced from a test using visible light. When a pixel difference exceeds a threshold, a defect is marked for the corresponding feature. The scope of embodiments is not limited to these test processes, as other test processes now known or later developed can be adapted for use in various embodiments.

Moving to FIG. 4, a comparison of three exemplary test recipes is given. The numbers in FIG. 4 are indicative of relative sensitivities for transmitted and reflected features. Recipe 1 has a substantially equal sensitivity to defects susceptible to imaging by transmitted light and defects susceptible to imaging by reflected light. Recipe 2 is more sensitive to transmitted light, whereas recipe 3 is more sensitive to reflected light. Recipe 2 may have a higher chance of producing false detections based on transmitted light. Recipe 3 may have a higher chance of producing false detections based on reflected light. In this example, all three recipes have been previously vetted to make sure that they are capable of detecting all real defects. In conventional systems, a user would choose one of the recipes to test a mask for defects, accepting that some false defects would be generated.

Figure 5:
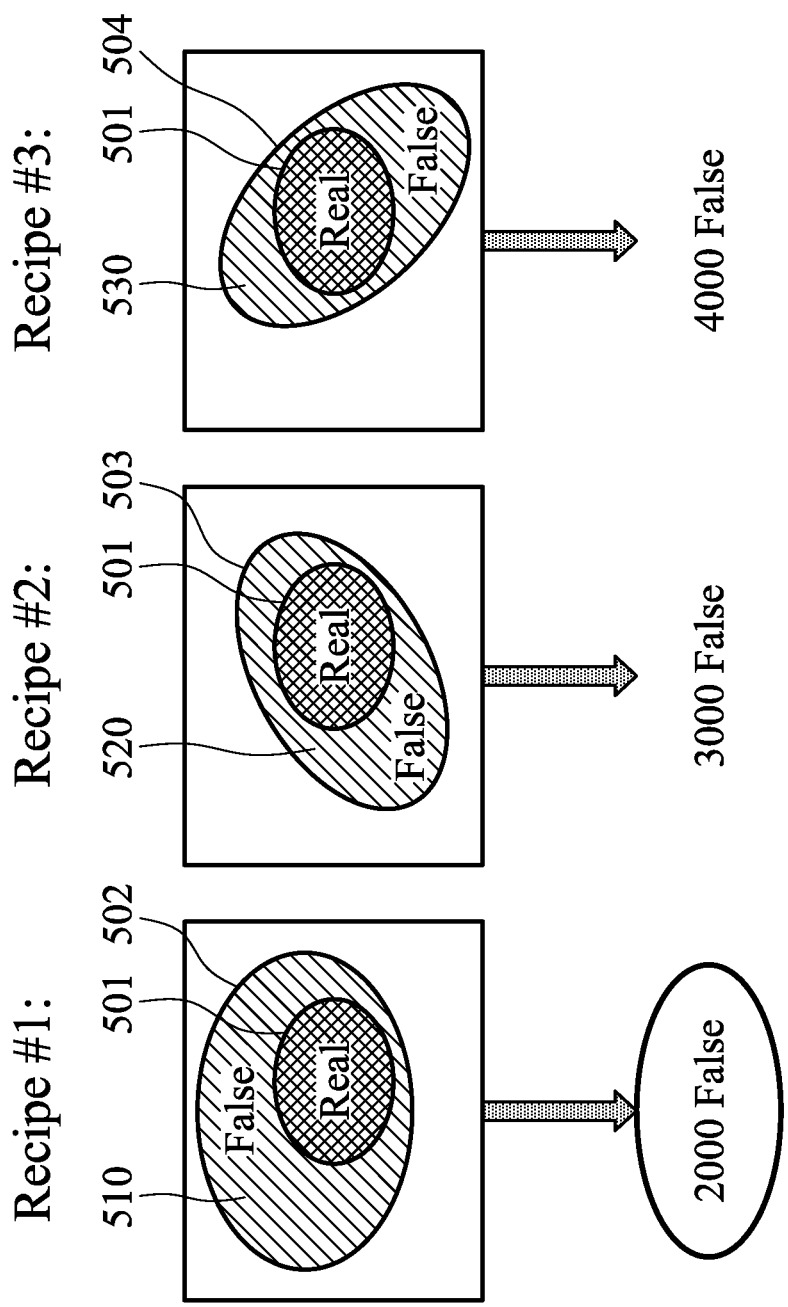
FIG. 5 gives another comparison of the test recipes shown in FIG. 4.

FIG. 5 gives another comparison of the test recipes shown in FIG. 4. Each of the recipes has a set of defects that it returns. For each of the recipes the set of real defects 501 is the same, since each of the recipes has been vetted for real defects. However, at the time of testing a newly-produced mask, a human may not know which of the defects are real and which are false.

The feature geometry used in a mask design will affect the ratio of real to false defect detections for a given recipe. For instance, some features within a mask design may be somewhat prone to causing false detections in a reflection test process, and other features may be prone to causing false defect detections in a transmitted light test process. In general, there is no perfect recipe, and all three recipes have weaknesses.

Recipe 1 has set 502 of defects, of which subset 501 are real, and subset 510 are false. For a mask of a particular size, recipe 1 in this example is expected to return about 2000 false defects. Recipe 2 has set 503 of defects, of which subset 520 are false defects, and for this example mask, it is expected to return about 3000 false defects. Recipe 3 has set 504 of defects, of which subset 530 of false defects, and for this example mask, it is expected to return about 4000 false defects. With this knowledge, an engineer may choose recipe 1 to minimize false defects in conventional systems. By contrast, for various embodiments of the disclosure, an engineer may use all three recipes as described further below.

Figure 6:
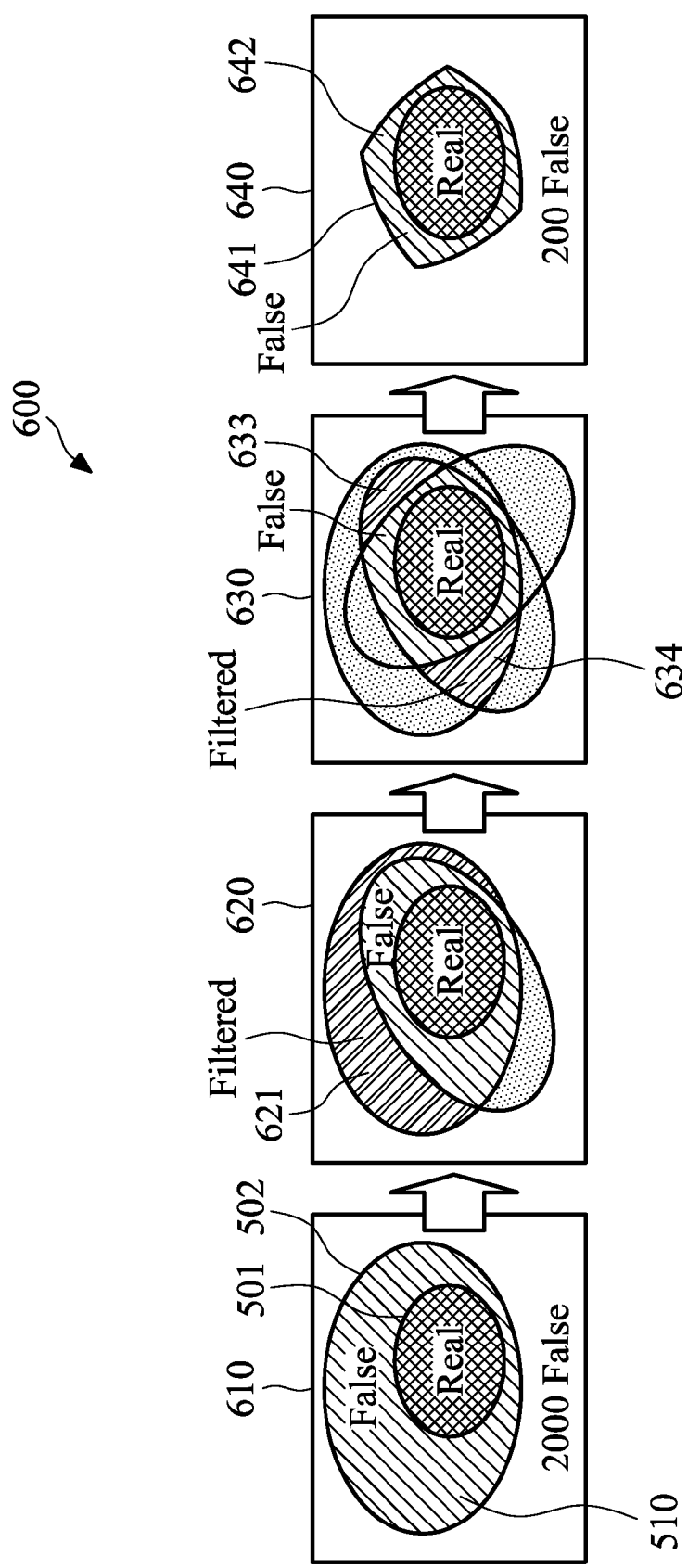
FIG. 6 is an illustration of an exemplary process for eliminating some false defect detections according to one embodiment.

FIG. 6 is an illustration of an exemplary process 600 for eliminating some false defect detections according to one embodiment. Block 610 illustrates the results of applying recipe 1 (FIG. 5) to an example mask where some features of the mask are marked as defective. In some embodiments, recipes 1, 2, and 3 are applied sequentially. The results are cascaded in the process of FIG. 6 to eliminate false defect detections.

In block 620, recipe 2 is applied only to those portions of the mask marked as defects by recipe 1. The subset of results 621 are reported by recipe 1 but not by recipe 2, and process 600 eliminates subset 621 as false.

In block 630, recipe 3 is applied to the defects remaining from block 620. Of the defects remaining after block 620, subsets 633, 634 are eliminated as false for not being reported by recipe 3.

Block 640 shows the results of cascading the three recipes. The entirety of defects left is represented by set 641, of which set 642 are false. In this example, the reduction in false defects is from about 2000 false defects to about 200 false defects, or about a ninety percent reduction.

Process 600 may be performed using known or off-the-shelf defect detection recipes and/or custom or later-developed recipes. Process 600 illustrates that while each of the three recipes has its own inadequacies, the results can be combined to produce a more accurate assessment of defects for a batch of masks.

In this example, it is not known at the time of testing which of the remaining defects 641 are real and which are false. Thus, after block 640, one or more human users inspect each of the identified defects. Defects confirmed as being false are disregarded. Defects confirmed as real are repaired through deposition, etching, or other processes. In some examples, further testing is performed after repair to confirm that all real defects are fixed. Once all defects are fixed, the mask may be delivered to a customer for use in producing semiconductor wafers.

Figure 7:
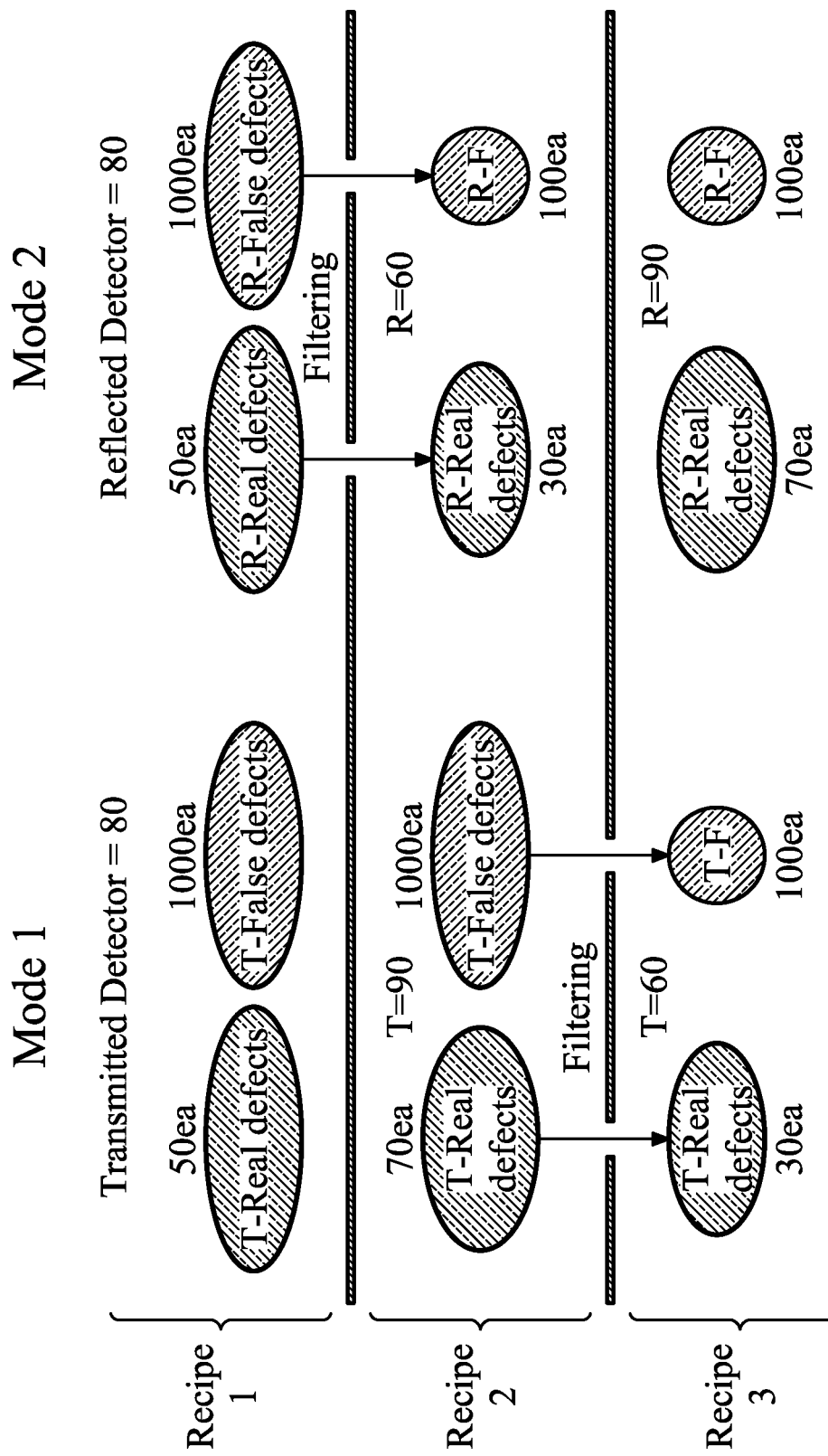
FIG. 7 is an illustration of the exemplary process of FIG. 6 showing how particular modes and sensitivities in recipes 1-3 affects filtering.

FIG. 7 is an illustration of exemplary process 600 (FIG. 6) showing how particular modes and sensitivities in recipes 1-3 affects filtering. Each of the recipes 1-3 has a transmitted light mode (shown as mode 1) and a reflected light mode (shown as mode 2).

In recipe 1, the transmitted light detector and the reflected light detector have approximately equal sensitivities to defects. The transmitted light detector indicates 50 real defects and one thousand false defects. Similarly, the reflected light detector indicates 50 real defects and one thousand false defects. Recipe 1 produces a total of 100 real defects and 2000 false defects.

In recipe 2, the sensitivity of the transmitted light detector is increased, and the sensitivity of the reflected light detector is decreased. For mode 1, since sensitivity is increased, the number of total defects increases (70 real and 1000 false). By contrast, the second mode shows a decrease in both real defects (30) and false defects (100). The reduction in sensitivity in mode 2 acts to filter some false defects in recipe 2. After recipe 2, the total number of real defects is still 100, and total number of false defects is reduced to 1100.

In recipe 3, the sensitivity of the reflected light detector is increased in mode 2, so there is no filtering with respect to mode 2 in recipe 3. On the other hand, the sensitivity of the transmitted light detector is decreased in recipe 3, relative to recipe 2, so that filtering is provided. For mode 1, the number of real defects is down to 30, and the number of false defects is down to 100. The total number of defects after recipe 3 is 100 real and 200 false.

Various embodiments are not limited to the modes shown in FIG. 7, as some embodiments may include fewer modes, more modes, or different modes from the specific embodiment illustrated in FIG. 7. For example, some embodiments may add a third mode for aerial defect detection.

Furthermore, some embodiments may include only one mode, which is sufficient to provide some amount of filtering. That is, even in one mode (transmitted light, reflected light or aerial), there exists many different algorithmic detectors that allow an engineer to set different settings and have different recipes to catch the same defect.

Figure 8:
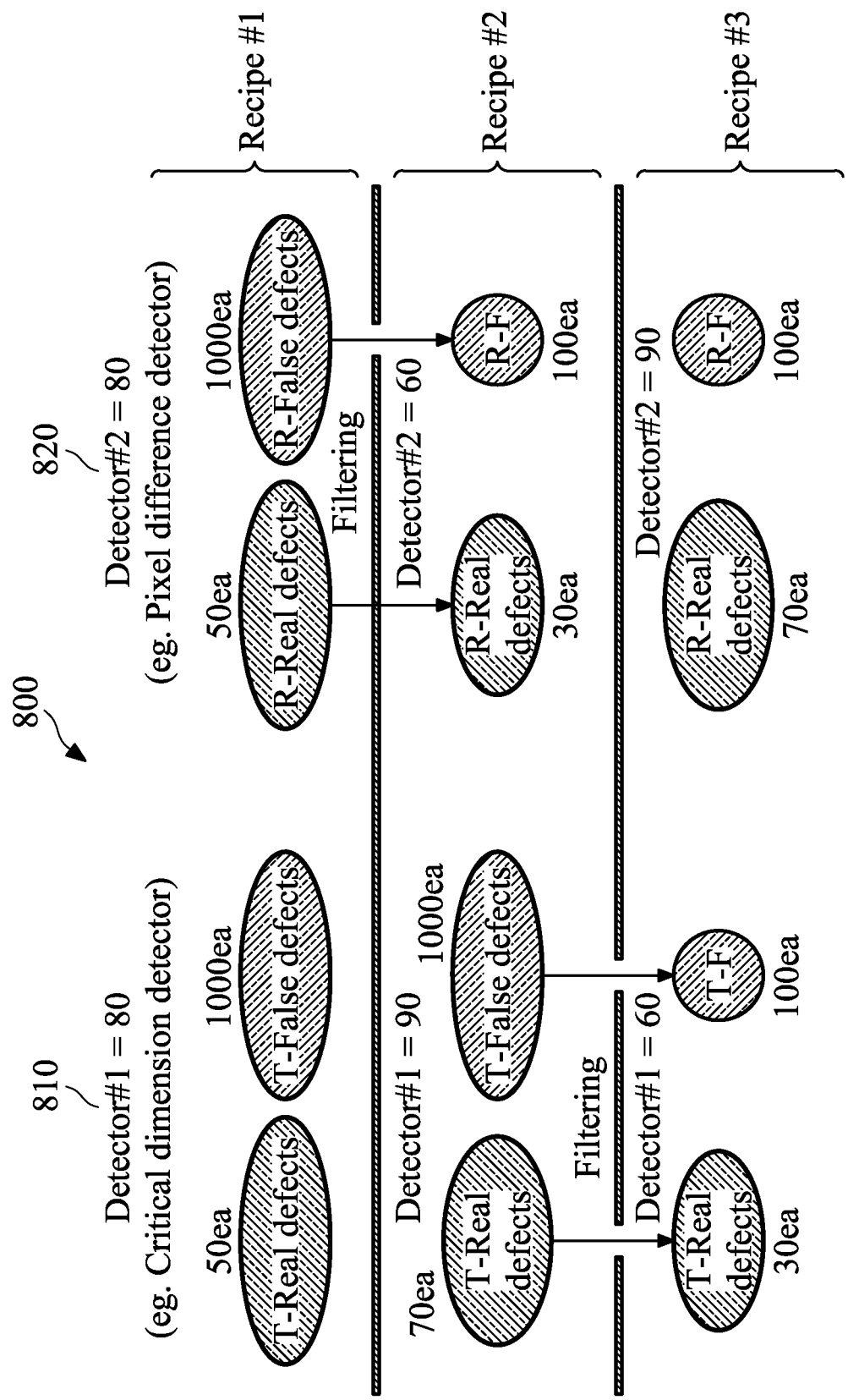
FIG. 8 is an illustration of an exemplary process showing defect detection in the context of a single mode.

FIG. 8 is an illustration of exemplary process 800 showing defect detection in the context of a single mode. Process 800 uses detectors 810 and 820, where detector 810 is, e.g., a critical dimension detector, and detector 820 is, e.g., a pixel difference detector. The recipes that are applied in this example use both detectors 810, 820 for the same mode—transmitted, reflected, aerial, or the like. Thus, recipes 1, 2, and 3 of FIG. 8 are different than the recipes of FIGS. 4-7. Process 800 uses the differences between critical dimension test processes and pixel difference test processes to eliminate false defect detections in a manner similar to that shown in FIG. 7. Hence, the sequential filtering of false defects illustrated in the examples above can be achieved using as few as one mode, or as many modes as appropriate for a given application.

Figure 9:
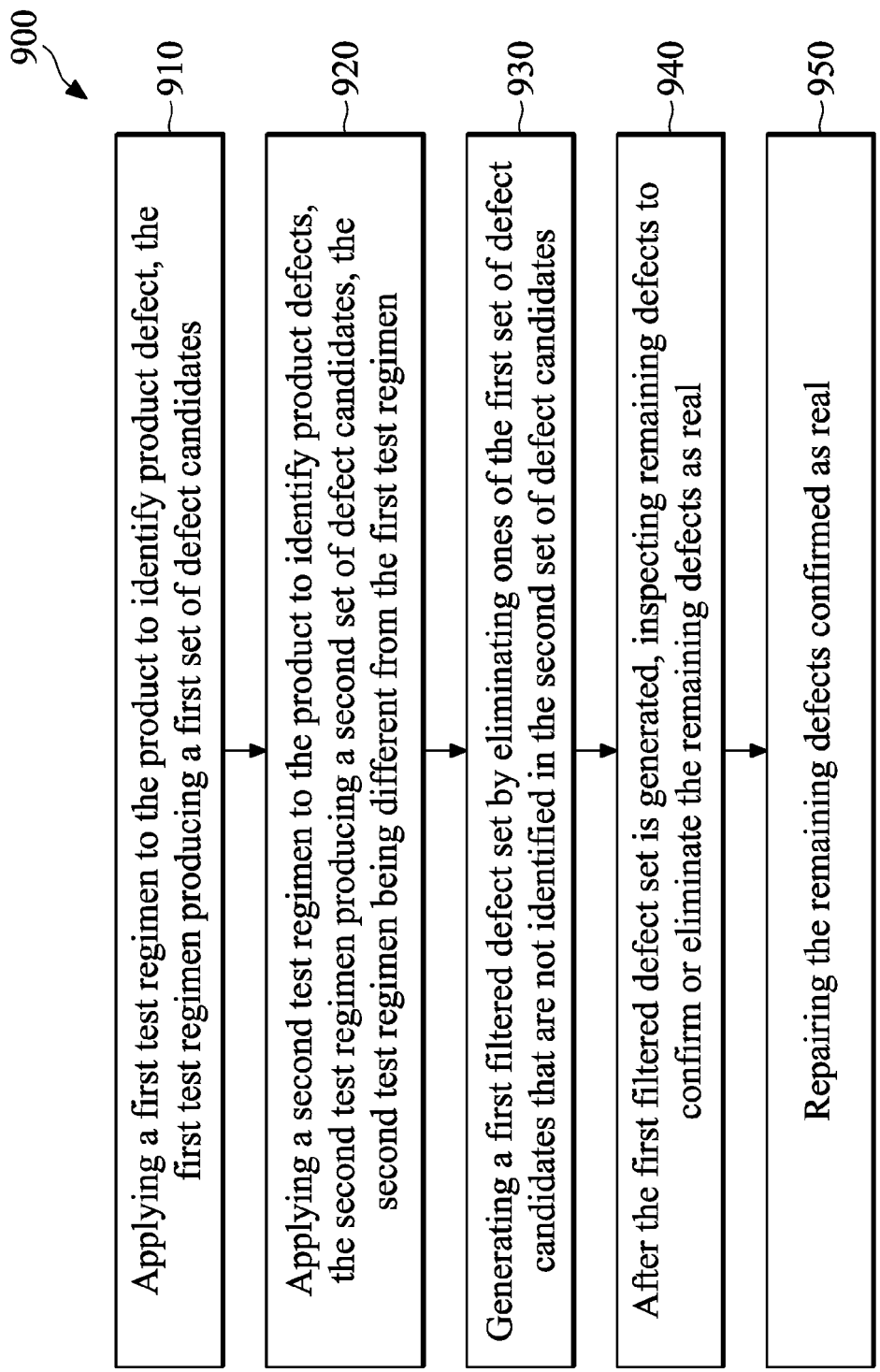
FIG. 9 is an illustration of an exemplary flow adapted according to one embodiment for eliminating false defects during manufacture of a product.

FIG. 9 is an illustration of exemplary flow 900 adapted according to one embodiment for eliminating false defects during manufacture of a product. Flow 900 may be performed, for example, by people and machines at one or more manufacturing facilities.

In block 910, a first test regimen is applied to the product to identify product defects, the first test regimen producing a first set of defect candidates. For example a test recipe capable of identifying real defects, and expected to produce a some false defects, may be used. Examples of types of recipes are described above.

In block 920, a second test regimen is applied to the product to identify product defects. The second test regimen produces a second set of defect candidates. In this example, the second test regimen is different from the first test regimen. For instance, each of the first and second test regimens may have different sensitivities and may be expected to return different numbers of false defects.

Each of the first and second regimens in this example include at least one test process to identify defects using visible light transmitted through a photomask and at least one test process to identify defects using visible light reflected from a photomask. However, the scope of embodiments is not limited thereto, as other embodiments may include test processes that do not use visible light or may not apply to photomasks at all.

In block 930, a first filtered defect set is generated by eliminating ones of the first set of defect candidates that are not identified in the second set of defect candidates. For instance, in one embodiment the defects identified by the first test regimen are provided to the second test regimen, and only the defects still identified by the second test regimen are kept.

In block 940, remaining defects are inspected to confirm or eliminate the remaining defects as real. In this example, the actions of block 840 are performed after the actions of blocks 910-930. Block 940 may include actions performed by humans to inspect the identified defects one-by-one to confirm or eliminate the defects still present after block 930.

In block 950, the remaining defects confirmed as real are repaired. For instance, various geometric structures on a photomask are confirmed as being defective. Manufacturing processes, such as electron beam writing and metal deposition, are then performed to correct the shape of the structure.

Various embodiments are not limited to the actions shown in flow 900. Other embodiments may add, omit, rearrange, or modify actions. For instance, other embodiments may further cascade additional test regimens to eliminate even more false defects. Moreover, other embodiments may include selecting two, three, or more test regimens to apply to the manufactured product. Test regimens may be selected in some instances by matching characteristics of the manufactured product to characteristics of the test regimens. For instance, in one example, test recipes for photomasks are selected by choosing test recipes that are expected to be appropriate for geometric structures known to be in the photomask.

Various embodiments may include advantages over other techniques. For instance, in many embodiments the time to perform a test recipe is much less than the time to perform human-operator inspection of identified defects. Thus, the human-operator time that is saved by eliminating false defects may greatly outweigh the time to perform one or more additional test recipes. Thus, some embodiments may save substantial amounts of time by eliminating false defects. Furthermore, many embodiments can be adapted to use existing test recipes and test hardware, thereby increasing throughput significantly without resulting in large capital outlays for implementation.

The foregoing has outlined features of several embodiments so that those skilled in the art may better understand the detailed description that follows. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions and alterations herein without departing from the spirit and scope of the present disclosure.

What is claimed is:

1. A method comprising:
    applying a first test with a first optical recipe to a manufactured product to identify a first set of product defect candidates, the first optical recipe having a higher sensitivity to transmitted light than to reflected light;
    applying a second test with a second optical recipe to the manufactured product to identify a second set of product defect candidates, the second optical recipe having a higher sensitivity to reflected light than to transmitted light; and
    generating a first filtered defect candidate set, the first filtered defect candidate set having only product defects found within both the first set of product defect candidates and the second set of product defect candidates.

2. The method of claim 1, further comprising:
    applying a third test with a third optical recipe to the manufactured product to identify a third set of product defect candidates, the third optical recipe being different than the first optical recipe and the second optical recipe; and
    generating a second filtered defect candidate set, the second filtered defect candidate set having only product defects found within each of the first set of product defect candidates, the second set of product defect candidates and the third set of product defect candidates.

3. The method of claim 2, wherein the third optical recipe has different light sensitivity settings than both the first optical recipe and the second optical recipe.

4. The method of claim 2, wherein the third optical recipe has similar sensitivity to transmitted light and reflected light.

5. The method of claim 1, further comprising, inspecting a defect within the first filtered defect candidate set to confirm that the defect is real.

6. The method of claim 5, further comprising, repairing the defect in response to determining that the defect is real.

7. The method of claim 1, wherein one of the first test and the second test comprises a pixel difference test.

8. The method of claim 1, wherein one of the first test and the second test comprises a critical dimension test.

9. The method of claim 8, wherein the critical dimension test uses visible light to examine contours produced from one of transmitted or reflected light.

10. A method comprising:
    applying a first test with a first optical recipe to a manufactured product to identify a first set of product defect candidates;
    applying a second test with a second optical recipe to the manufactured product to identify a second set of product defect candidates, wherein the first optical recipe and the second optical recipe have different sensitivities to reflected and transmitted light; and
    generating a first filtered defect candidate set, the first filtered defect candidate set having only product defects found within both the first set of product defect candidates and the second set of product defect candidates.

11. The method of claim 10, wherein, the first optical recipe has a higher sensitivity to transmitted light than to reflected light.

12. The method of claim 10, wherein, the second optical recipe has a higher sensitivity to reflected light than to transmitted light.

13. The method of claim 10, further comprising:
applying a third test with a third optical recipe to the manufactured product to identify a third set of product defect candidates, the third optical recipe having a similar sensitivity to reflected light as to transmitted light; and
generating a second filtered defect candidate set, the second filtered defect candidate set having only product defects found within each of the first set of product defect candidates, the second set of product defect candidates and the third set of product defect candidates.

14. The method of claim 10, wherein one of the first test and the second test comprises a pixel difference test.

15. The method of claim 10, wherein one of the first test and the second test comprises a critical dimension test.

16. The method of claim 15, wherein the critical dimension test uses visible light to examine contours produced from one of transmitted or reflected light as the visible light interacts with features on the manufactured product.

17. A method comprising:
applying a first test with a first optical recipe to a manufactured product to identify a first set of product defect candidates, the first optical recipe having a higher sensitivity to transmitted light than to reflected light;
applying a second test with a second optical recipe to the manufactured product to identify a second set of product defect candidates, the second optical recipe having a higher sensitivity to reflected light than to transmitted light; and
applying a third test with a third optical recipe to the manufactured product to identify a third set of product defect candidates, the third optical recipe having a similar sensitivity to reflected light as to transmitted light; and
generating a filtered defect candidate set, the filtered defect candidate set having only product defects found within each of the first set of product defect candidates, the second set of product defect candidates and the third set of product defect candidates.

18. The method of claim 17, further comprising:
inspecting a defect within the first filtered defect candidate set to confirm that the defect is real; and
repairing the defect in response to determining that the defect is real.

19. The method of claim 17, wherein the first test comprises a pixel difference test that compares a reference grayscale pixel map with a pixel map produced from visible light used by the first test.

20. The method of claim 17, wherein the first test comprises a critical dimension test that uses visible light to examine contours produced from one of transmitted or reflected light as the visible light interacts with features on the manufactured product.

* * * * *